United States Patent
Crook et al.

(10) Patent No.: US 10,472,606 B2
(45) Date of Patent: Nov. 12, 2019

(54) CELL PRESERVATION METHOD FOR PLURIPOTENT STEM CELLS

(71) Applicant: ES CELL INTERNATIONAL PTE LTD., Helios Block (SG)

(72) Inventors: Jeremy M. Crook, Wollongong (AU); Lucy Kravets, Melbourne (AU)

(73) Assignee: ES Cell International Pte Ltd, Singapore (SG)

(*) Notice: Subject to any disclaimer, the term of this patent is extended or adjusted under 35 U.S.C. 154(b) by 0 days.

(21) Appl. No.: 15/617,892

(22) Filed: Jun. 8, 2017

(65) Prior Publication Data
US 2017/0275588 A1    Sep. 28, 2017

Related U.S. Application Data

(62) Division of application No. 11/628,443, filed as application No. PCT/AU2005/000783 on Jun. 2, 2005, now Pat. No. 9,714,412.

(30) Foreign Application Priority Data

Jun. 2, 2004 (AU) ............... 2004902933
May 18, 2005 (AU) ............... 2005902548

(51) Int. Cl.
  *C12N 5/0735* (2010.01)
  *A01N 1/02* (2006.01)

(52) U.S. Cl.
  CPC ............ *C12N 5/0606* (2013.01); *A01N 1/02* (2013.01); *A01N 1/0284* (2013.01)

(58) Field of Classification Search
  None
  See application file for complete search history.

(56) References Cited

U.S. PATENT DOCUMENTS 7,811,819 B2  10/2010  Ware et al.
9,714,412 B2  7/2017  Crook et al.

FOREIGN PATENT DOCUMENTS

| EP | 0246824 A2 | 11/1987 |
|----|---|---|
| GB | 2330516 A | 4/1999 |
| WO | 1996/24018 A1 | 8/1996 |
| WO | 2001/68815 A1 | 9/2001 |
| WO | 2004/010780 A2 | 2/2004 |
| WO | 2004/098285 A2 | 11/2004 |

OTHER PUBLICATIONS

Freshney, Culture of Animal Cells, A Manual of Basic Techniques adn Specialized Applications, sixth edition. John Wiley & Sons, Inc., Hoboken, New Jersey. p. 328, (2010).
Fujioka et al., A simple and efficient cryopreservation method for primate embryonic stem cells. Int J Dev Biol. Dec. 2004;48(10):1149-54.
Leibo et al., Effects of freezing on marrow stem cell suspensions: interactions of cooling and warming rates in the presence of PVP, sucrose, or glycerol. Cryobiology. Jan.-Feb. 1970;6(4):315-32.
Reubinoff et al., Effective cryopreservation of human embryonic stem cells by the open pulled straw vitrification method. Hum Reprod. Oct. 2001;16(10):2187-94.
Richards et al., An efficient and safe xeno-free cryopreservation method for the storage of human embryonic stem cells. Stem Cells. 2004;22(5):779-89.
Walters et al., The history of sperm cryopreservation. Sperm Banking: Theory and Practice. Allan A. Pacey (Ed.), Cambridge University Press. Chapter 1, pp. 1-10, (2009).

*Primary Examiner* — Blaine Lankford
(74) *Attorney, Agent, or Firm* — McCarter & English, LLP; Jonathan M. Sparks; Wendy Thai

(57) ABSTRACT

The present invention provides a method for freezing a stem cell or a cell derived therefrom, the method including the steps of providing a cell suspension, performing ice nucleation on the cell suspension, and lowering the temperature of the ice nucleated cell suspension to a temperature sufficiently low to allow long term storage of the stem cell. The method is preferably used for the cryopreservation of human embryonic stem cells.

19 Claims, 12 Drawing Sheets

Bright Field

Oct-4

TRA 1-60

TRA 1-81

CELL PRESERVATION METHOD FOR PLURIPOTENT STEM CELLS

CROSS-REFERENCE TO RELATED APPLICATIONS

This application is a divisional application of U.S. patent application Ser. No. 11/628,443, filed on May. 25, 2007, issued as U.S. Pat. No. 9,714,412 on Jul. 25, 2017, incorporated herein by reference in its entirety, which claims priority to, and the benefit of PCT international application number PCT/AU2005/00783 filed on May 25, 2007, incorporated herein by reference in its entirety, which claims priority to, and the benefit of, Australian provisional patent application serial number 2005902548 filed on May 18, 2005 and Australian provisional patent application serial number 2004902933 filed on Jun. 2, 2004, both of which are incorporated herein by reference in their entireties. Priority is claimed to each of the foregoing applications.

The above-referenced PCT international application was published as PCT International Publication No. WO/2005/118785 on Dec. 15, 2005, which publication is incorporated herein by reference in its entirety.

FIELD

The present invention relates to a method of preserving cells by freezing. More specifically, the method is useful for the cryopreservation of stem cells.

BACKGROUND

Long-term storage of animal cells and tissues is of widespread critical importance to the research and biomedical fields. Cryopreservation of cells and tissues is useful, for the long-term storage of cell lines to provide an unchanging population of cells; and the storage of populations of cells for research or medical purposes.

It is widely held that animal cells can be stored indefinitely once they reach liquid nitrogen temperature (−196° C.). It has been well-established, however, that the freezing process itself results in immediate and long-term damage to cells with the greatest damage occurring to cells as they traverse the intermediate zone of temperature (−15° C. to −60° C.) during cooling and thawing (Mazur, Am. J. Physiol., 247:C125-142, 1984). The primary damaging physical events that can occur to cells during the process of freezing include dehydration and intracellular ice crystal formation. During freezing, solute is rejected from the solid phase producing an abrupt change in concentration in the unfrozen portion of solution. A biological cell responds to this perturbation by dehydrating to reach a new equilibrium state between intracellular and extracellular solutions. At high cooling rates, equilibrium cannot be maintained because the rate at which the chemical potential in the extracellular solution is being lowered is much greater than the rate at which water can diffuse out of the cell. The end result of this imbalance is that intracellular ice formation is observed which is lethal to the cell (Toner, J. of Applied Phys., 67:1582-1593, 1990). At low cooling rates, cells are exposed for long periods of time at high subzero temperatures to high extracellular concentrations resulting in potentially damaging high intracellular concentrations (Lovelock, Biochem. Biophys. Acta, 10:414-446, 1953).

There have been attempts in the art to incorporate the process of vitrification into methods of cryopreserving cells. The aim of vitrification is to lower the temperature of a cell suspension while avoiding the formation of ice crystals by the use of viscous or concentrated liquid solutions. This approach is fundamentally different to standard methods of freezing that concentrate more so on carefully controlling the formation of ice crystals Methods incorporating vitrification have shown some promise however recoveries can be poor. Furthermore, the methods are not amenable to automation, and therefore quality control can be difficult. Another problem is that compounds such as polyethylene glycol are required in the vitrification solution. A further problem with vitrification is that the vessels used severely limit the amount of material that can be frozen. Additionally, the commonly used "open straws" do little to avoid the possibility of microbial cross-contamination of the materials to be frozen.

The clinical and commercial application of cryopreservation for certain cell types is limited by the ability to recover a significant number of total viable cells that function normally. Significant losses in cell viability are observed in certain primary cell types. Examples of freeze-thaw cellular trauma have been encountered with cryopreservation of hepatocytes (Borel-Rinkes et al., Cell Transplantation, 1:281-292, 1992) porcine corneas (Hagenah and Bohnke, 30:396-406, 1993), bone marrow (Charak et al., Bone Marrow Transplantation, 11:147-154, 1993), porcine aortic valves (Feng et al., Eur. J. Cardiothorac. Surg., 6:251-255, 1992) and human embryonic stem cells (hESCs; http://www.wicell.org/forresearchers, FAQs—Culturing Human ES Cells: FAQs 4 & 8; Reubinoff et al., Human Reprod, 16(10):2187-2194, 2001).

The regulatory requirements for producing clinically acceptable hESCs present unique characteristics and accompanying challenges. For example, for a hESC to be useful in routine therapeutic applications it will be necessary to generate and store cells in a Master Cell Bank from a single hESC source. Compliance will ensure quality assurance and safety towards maximizing clinical efficacy, the primary mandate for the Food and Drug Administration (FDA). A suitable cryopreservation method that satisfies existing and future regulations under Good Tissue Practice (GTP) and Good Manufacturing Practice (GMP) will be essential to the manufacture and use of viable material for cell based therapy. Thus, a standardized procedure with validated components, free from sensitising reagents such as certain animal sera and selected proteins, performed under conditions designed to minimize contamination with adventitious agents, and amenable to high throughput processing for production of large cell banks is a necessary prerequisite.

Cryopreservation protocols typically require the use of cryoprotective agents ("CPAs") to achieve improved survival rates for animal cells. A variety of substances have been used or investigated as potential additives to enhance survival of cells in the freezing process. Other substances used include sugars, polymers, alcohols and proteins. CPAs can be divided roughly into two different categories; substances that permeate the cell membrane and impermeable substances. One mechanism of protection results from reduction in the net concentration of ionic solutes for a subzero temperature when a CPA is present. This colligative effect is true for all substances that act as a CPA (Fahy, Biophys. J. 32:837-850, 1980). The addition of a CPA however, changes the ionicity of the solution. Both tissues and intact organs can exhibit reduced cellular viability when exposed to sufficiently large step changes in external osmolarity produced by introduction of a freezing solution (Pegg, Cryobiology, 9:411-419, 1972). In addition, long term exposure to even low concentrations of certain CPAs at room temperature is potentially damaging (Fahy, Cryobiology, 27: 247-268, 1990).

Another media component routinely added to freezing media to reduce cell damage and death during freezing and thawing is serum. This additive, however, is highly complex and may add a number of factors (known and unknown), which may interfere with or alter cell function. Other non-permeating protective agents such as ethylene glycol, polyvinyl pyrrolidone (Klebe and Mancuso, In Vitro, 19:167-170, 1983) sucrose, and culture medium (Shier and Olsen, In Vitro Cell Dev. Biol., 31:336-337, 1995), have been studied for their effectiveness as cryoprotective agents for cells with variable results.

U.S. Pat. No. 4,004,975 to Lionetti et al. discloses the cryopreservation of leukocytes from centrifuged blood in a solution of hydroxyethyl starch and dimethylsulfoxide. U.S. Pat. No. 5,071,741 to Brockbank and PCT WO 92/08347 to Cryolife, published May 29, 1992, disclose the use of algae-derived polysaccharides such as agarose and alginate in a cryoprotective cell medium. U.S. Pat. No. 5,405,742 to Taylor discloses a solution for use as a blood substitute and for preserving tissue that includes dextran.

PCT WO 95/06068 discloses the use of polysaccharides to improve hematopoietic functions and serve as a radioprotective agent. The use of gum arabic, cherry resin and apricot resin in ewe semen freezing medium is disclosed in Platov et al. (Ovtsevodstvo, 10:38-39, 1980, abstract). Holtz et al. (Proc. Fourth Intern. Symp. Repr. Phys. Fish, 1991) discloses the use of saccharides such as glucose and sucrose in the cryopreservation of trout semen. Hill et al. (J. Lab. Clin. Med., 111:73-83, 1988) discloses the use of arabinogalactan to obtain washed murine platelets by centrifugation. Maisse (Aquat. Living Resour., 7:217-219, 1994) discloses a study of the effect of carbohydrates such as glucose and maltose on the cryopreservation of trout sperm. Isotonic sucrose in combination with calf serum has been used in a medium for the cryopreservation of animal cells (Shier and Olsen, In Vitro Cell. Dev. Biol., 31:336-337, 1995).

Even in consideration of the many years of research in the field of cryopreservation, there is still a need in the art for alternative and improved methods and compositions for freezing cells. There is a special need for methods suitable for hESCs. hESCs have the potential to develop into all or nearly all of the more than 200 cell types in the human body. They have much therapeutic value for treating disease and regenerating damaged tissues and organs. Their clinical potential, however, hinges on their ability to be easily and reliably passaged, frozen, transported, stored and used.

Like many cells used in biomedical research, embryonic stem cells are currently stored and transported in a cryopreserved state in a liquid nitrogen bath. When researchers thaw the cells for use in the lab, however, less than 1% remain viable. The few surviving cells must be placed in culture and painstakingly tended to for weeks before new colonies are abundant enough to be useful for experiments or therapy. The low survival rate makes working with the stem cells time and labour intensive. Furthermore because so few cells survive freezing, natural selection may be altering cell lines in unknown and undesired ways.

In addition, to satisfy existing and future requirements for GTP and GMP and provide quality assurance for the therapeutic utility of stem cells, there is a need for a cryopreservation method with validated components, free from sensitising reagents such as certain animal sera and selected proteins, performed under conditions designed to minimize contamination with adventitious agents, and amenable to high throughput processing for production of cell banks.

It is therefore an aspect of the invention to overcome a problem of the prior art to provide improved methods for the cryopreservation of stem cells, ensuring suitable post-freeze/thaw cell viability and cell quality for the therapeutic utility of stem cells.

The discussion of documents, acts, materials, devices, articles and the like is included in this specification solely for the purpose of providing a context for the present invention. It is not suggested or represented that any or all of these matters formed part of the prior art base or were common general knowledge in the field relevant to the present invention as it existed in Australia before the priority date of this application.

SUMMARY OF THE INVENTION

Stem cells are primitive cells known in the art for their ability to differentiate into mature functional cells of the body. Accordingly, these cells are proposed to have use in therapy of the human body in diseases where the subject's own cells are deficient, damaged or simply not present. Thus, where a replacement cell is required, a stem cell may be used as a starting point for generating the mature cell, tissue or organ required. For this scenario to become a reality in the clinic it is necessary to provide methods for cryopreserving stem cells.

Accordingly, in a first aspect the present invention provides a method for freezing a stem cell or a cell derived therefrom, the method including the steps of providing a cell suspension, performing ice nucleation on the cell suspension, and decreasing the temperature of the ice nucleated cell suspension to a temperature sufficiently low to allow long term storage of the stem cell. Applicants have found that by decreasing the temperature of a cell suspension in the manner defined above, cells of enhanced viability are provided after thawing.

The methods for cryopreservation described herein are particularly amenable to implementation using a programmable freezer. This automated approach typically provides a consistent outcome in terms of cell quality that can be validated for compliance with the code of Good Manufacturing Practice, which is a component of the regulatory package that would be required for registration with an authority such as the FDA. Importantly, the Applicant has shown that cryopreservation can be achieved without the use of exogenous biological material as a cryoprotectant. Serum is often included in liquid medium used for freezing cells, however due to the inherent problems in standardising serum difficulties may arise in registering a therapeutic including this biological. The method is particularly advantageous for an embryonic stem cell and a progenitor cell that is partially differentiated and derived from an embryonic stem cell. More particularly the present application demonstrates that human ESCs can be frozen for extended periods of time and upon thawing retain important characteristics of such as viability and pluripotency.

Also provided by the present invention are frozen and thawed cells produced by the methods of the invention, as well as pharmaceutical compositions incorporating the cells, and methods of treatment using the cells.

DETAILED DESCRIPTION OF THE INVENTION

Figure 1:
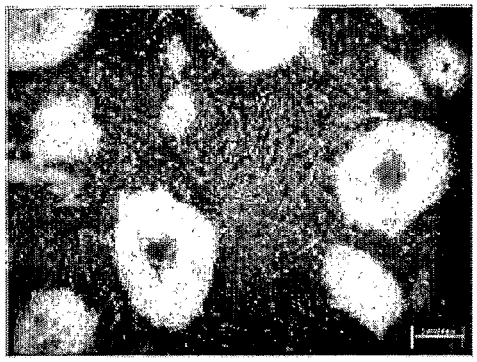
FIG. 1 shows post-frozen/thaw hESC recovery at day 8 of culture. Representative photomicrographs of bright field images and Oct-4, TRA 1-60 and TRA 1-81 labelling of post frozen/thaw hES-2 cells illustrate recovery following freezing, thaw and reculture. Left and right panels represent replicate cultures.
Figure 1:
Figure 1:
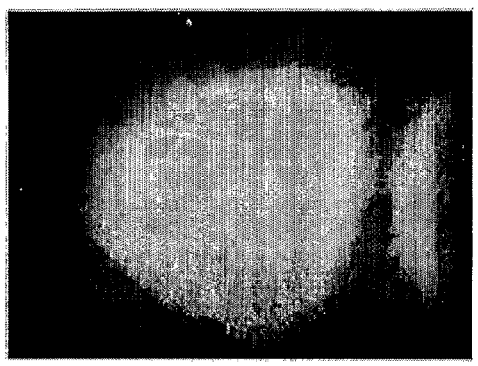
Figure 1:
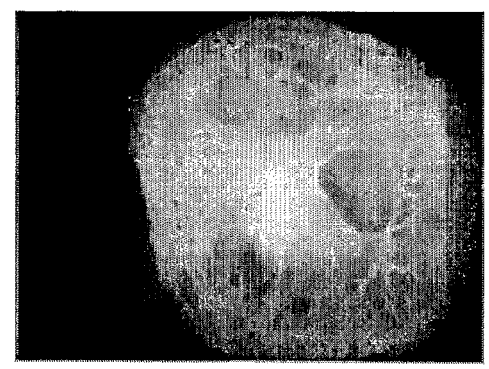
Figure 1:
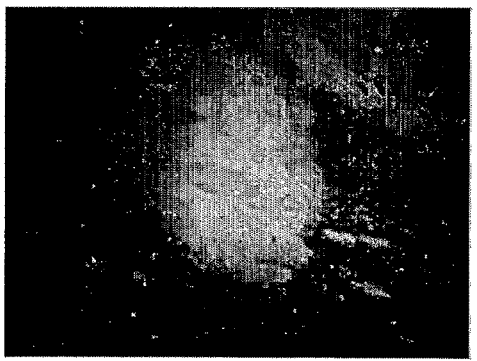
Figure 1:
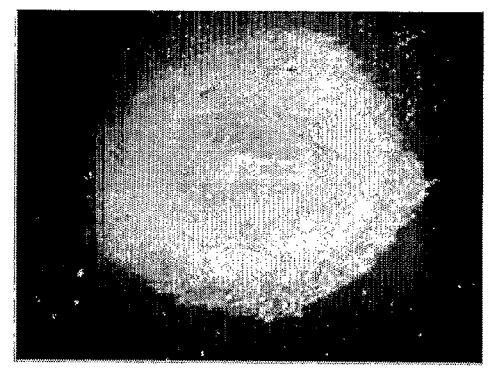
Figure 1:
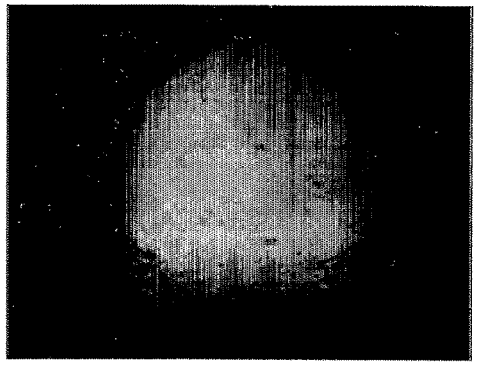
Figure 1:

In a first aspect the present invention provides a method for freezing a stem cell or a cell derived therefrom, the method including the steps of providing a cell suspension, performing ice nucleation on the cell suspension, and decreasing the temperature of the ice nucleated cell suspension to a temperature sufficiently low to allow long term storage of the stem cell.

The applicant has found that the method is surprisingly effective in preserving stem cells for extended periods of time. The method may be carried out manually, however it is preferably carried out using a freezer capable of executing a freezing program.

Upon thawing of the cells, it is found that many cell parameters are substantially unchanged, such as viability and the ability to differentiate under appropriate stimulus. This is in contrast to methods described in the prior art that have deleterious effects (Reubinoff et al., Human Reprod, 16(10):2187-2194, 2001; Richards et al., Stem Cells. 2004; 22(5):779-89).

The starting material for cryopreservation is generally a stem cell culture taken from a laboratory incubator. In terms of preparation for freezing, the cells may be disaggregated to form a suspension by either enzymatic or mechanical means (see FIG. 4). Similarly, passaging after thawing can be achieved mechanically (see FIG. 5).

The skilled person will understand that there are many standard methods for preparing a cell suspension for the purposes of freezing or further passaging the cells. However in a preferred form of the method the cells are prepared by a method including the steps of exposing a cell culture or aggregate to an amount of collagenase for a length of time sufficient to produce cell clumps, exposing the cell clumps to an excess volume of hESC media, disrupting the cell clumps mechanically to generate uniform size cell clumps, pelleting the cell aggregates and resuspending the cells in a solution containing a cryoprotectant. In a preferred form of the method the solution is substantially devoid of extraneous biological material such as serum. Indeed, the ability to successfully cryopreserve cells is an advantage of the present invention. It is very difficult to register a biological for clinical use if it includes or has been in contact with an undefined substance such as animal serum. Substances such as serum may also contain pathogens such as bacteria and viruses. In a preferred form of the method the solution is the same as or similar to CryoStor™ CS5 or CryoStor™ CS10 solutions. CryoStor™ CS5 solution contains a final concentration of 5% DMSO as a cryoprotectant, which can be further augmented by the addition of further DMSO to achieve a final concentration of 10%. Alternatively, CryoStor™ CS10 can be employed, which already comprises a final concentration of 10% DMSO. The presently described preferred freezing solutions are FDA approved for utilization in cell therapy and tissue engineering arena.

As a precursor step to ice nucleation, the cell suspension may be subjected to a "cold activation step". This typically involves cooling the suspension to a temperature from about −4° C. to about −12° C. Preferably the suspension is cooled to about −8° C. at a rate of about −1° C./min for the cold activation step. A "soak" step may then follow whereby the cell suspension is maintained at the temperature used for cold activation (typically −8° C.) for a period of from about 5 min to about 10 min.

Following the "cold activation step" to achieve thermal equilibrium, ice nucleation is initiated. Ice nucleation occurs by decreasing the temperature of a cell sample to a nucleating point. Following ice nucleation, the temperature of the cell sample is lowered from the nucleating point to the solidification point.

Where a programmable freezer is used to implement the method, the ice nucleation step is performed by providing appropriate instructions to the freezer. Preferably the ice nucleation step is performed by lowering the temperature of the cell suspension from the temperature at the conclusion of the cold activation step to a temperature of about −10° C. to about −12° C. More preferably the temperature is lowered to about −10.9° C. The temperature is typically lowered rapidly at a rate of from about −15° C./min to about −55° C./min. More preferably the rate is about −35° C./min to about −38° C./min.

In one form of the invention the ice nucleation step includes lowering the temperature of the cell suspension to a temperature of from about −11° C. to about −13° C. Preferably the temperature is lowered to a temperature of about −12.1° C. Typically, the rate at which the temperature is lowered is from about −5° C./min to about −15° C./min. Preferably the rate is −9° C./min. At the end of the ice nucleation step the temperature of the cell suspension is typically about −12.1° C.

In another embodiment of the method the ice nucleation step is performed manually. Where a programmable freezer is used, the manual ice nucleation step may be performed by halting the programmed sequence of the freezer at an appropriate point, removing the straw containing the cell suspension, touching the straw with liquid nitrogen-cooled forceps, returning the straw to the freezer, and instructing the freezer to resume the freezing program. The skilled person will be able to identify other means and contrivances to achieve ice nucleation manually, all being included in the scope of the present application.

One possible freezer program to accommodate manual ice nucleation is shown in Example 2. Alternatively, ice nucleation may be performed automatically by the freezer program. This may be done by programming further steps into the freezer program such as those described in steps 4 to 8 of the program described in Example 3.

It will be understood that the present method may include a period where the cell suspension is left to incubate for a period of time to allow a given process to at least partially complete. For example, following the ice nucleation step the cell suspension may be kept at the temperature at which ice-nucleating is performed to allow the formation of an adequate seed or seeds in the cell. In a preferred form of the method, a period of about 5 min is allowed for adequate seed or seeds to form before proceeding with further cooling.

After the ice nucleation step the method may include a dehydration step whereby the temperature of the cell suspension is lowered to a temperature of from about −35° C. to about −38° C. This decrease in temperature is often achieved relatively slowly, and is typically implemented at about −0.8° C./min.

After the ice nucleation or dehydration step, the suspension is typically further decreased rapidly to a temperature of about −180° C. for long term isolation and storage in liquid nitrogen.

Without wishing to be limited by theory, it is proposed that where the rate of cooling is too low, cell death arises through extended periods of exposure to hypertonic conditions. Accordingly, by increasing the rate of cooling, the exposure time to hypertonic conditions is decreased along with a concomitant reduction in cell damage. Where the rate of cooling is too fast, cell death arises through intracellular ice formation. Therefore, a preferred rate of cooling may be considered as the most rapid rate of cooling without intracellular ice formation.

The skilled person will understand that the method may include other steps including further temperature manipulation or the addition of reagents.

The present invention has particular applicability to the cryopreservation of mammalian stem cells. Stem cells have two important characteristics that distinguish them from other types of cells. First, they are unspecialized cells that renew themselves for long periods through cell division. The second is that under certain physiologic or experimental conditions, they can be induced to become cells with special functions such as a heart muscle cell or an insulin-producing cell of the pancreas.

In a more preferred form of the invention the stem cell is an embryonic stem cell, which are cultured from cells obtained from the inner cell mass of an embryo. Embryonic stem cells and are pluripotent, having the potential to develop into nearly all of the tissues in the body. This class of cell appears to have no equivalent cell type in vivo, and is proposed to be a tissue culture artefact (reviewed by Zwaka and Thompson, 2005, Development 132(2), 227-233). Embryonic stem cells are known to exhibit a number of properties that are simply not seen in the intact embryo. For example, although embryonic stem cells retain properties of early embryonic cells in vitro, no pluripotent cell demonstrates long term self-renewal in vivo. Embryonic cells, once brought into tissue culture, are exposed to numerous extrinsic signals to which they would never be exposed in vivo. Other workers have shown that ES cells adapt to tissue culture conditions and acquire novel functions that allow them to proliferate in an undifferentiated state indefinitely (Buehr and Smith, 2003, Philos Trans R Soc Lond B Biol Sci 358, 1397-1402; Rossant, 2001, Stem Cells 19, 477-482; Smith, 2001, Annu Rev Cell Dev Biol 17, 436-462). Still more preferably the stem cells are hESCs. As discussed elsewhere herein, there is great potential for the therapeutic use of embryonic stem cells for the treatment of human disease.

Figure 12:
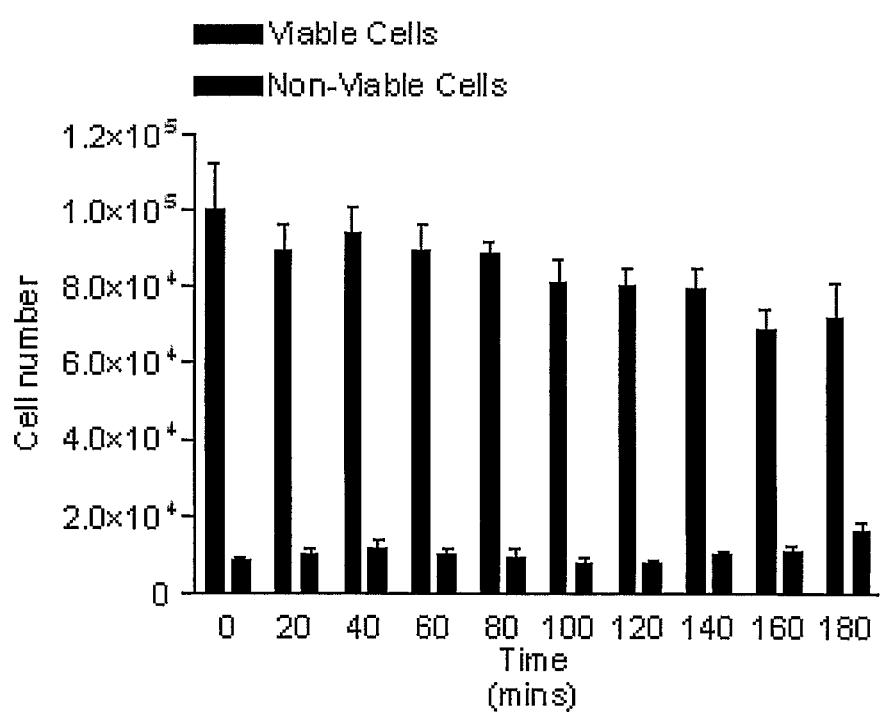
FIG. 12 shows efficacy of cryopreservation medium for maintaining pre-frozen hESC viability. Representative profiling of hESC illustrates viability over time (0-3 hours) while stored at 4° C. in cryopreservation medium. Data are presented as viable and non-viable cell numbers over time, and are taken from 3 separate studies.

Applicants have found that by implementing the cryopreservation methods described herein, cells of improved quality are provided for freezing and after thawing when compared with methods of the prior art. In one form of the method, viability of cells prepared for freezing may be measured by monitoring the number of cells still living as a function of time after exposure to a temperature of 4° C. By this measure, greater than about 90% of the cells that were living immediately after preparing them for freezing prior to freezing were still living after 1 hour at 4° C. (see FIG. 12). Another preferred form of the method provides that about 75% of the cells that were living immediately after thawing were still living after 3 hours at 4° C. (see FIGS. 12).

Figure 6:
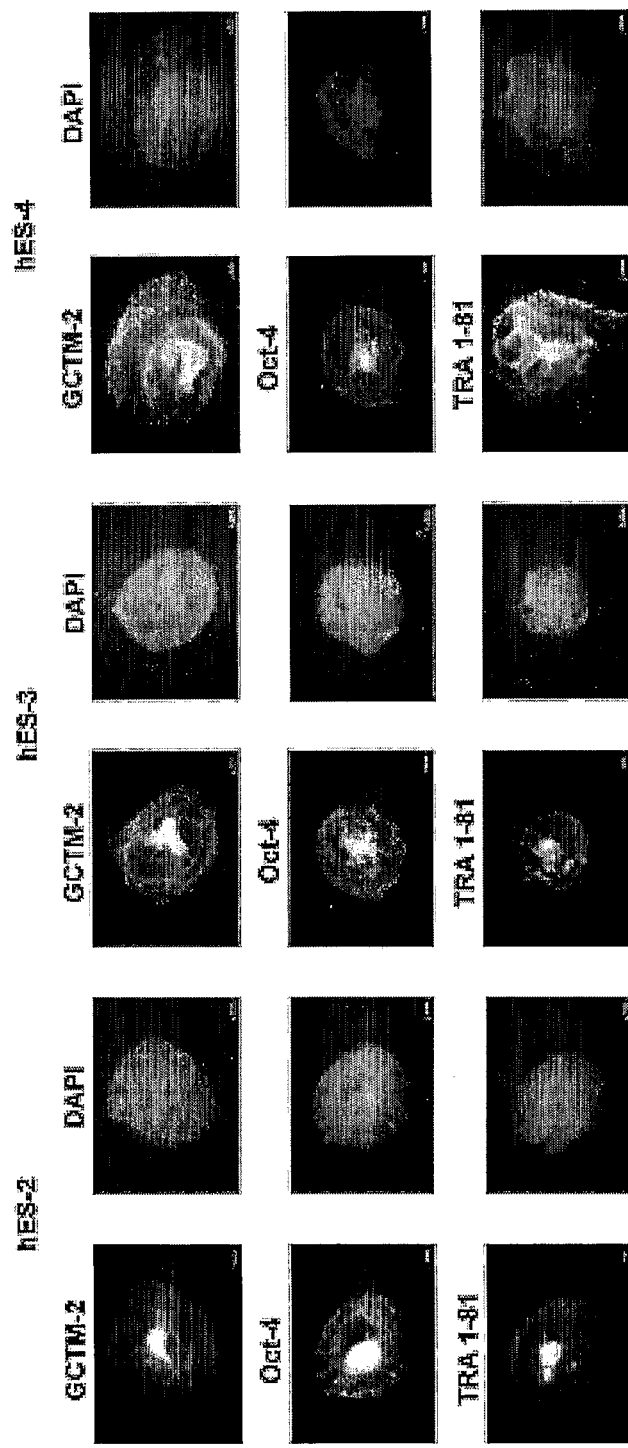
FIG. 6 shows post-frozen/thaw recovery of multiple hESC lines maintained through multiple passages. Representative photomicrographs of GCTM-2, Oct-4 and TRA 1-81 labelling of post frozen/thaw hES-2, hES-3, and hES-4 cells illustrate cell recovery following freezing, thaw and reculture.

Another advantage of the invention is that upon thawing the cells retain pluripotency, retaining an undifferentiated phenotype. As will be noted in FIG. 1, after thawing hESCs, the cells maintained characteristics of undifferentiated cells. The cells exhibited non-cystic growth and expressed Oct-4, TRA 1-60 and TRA 1-81. FIG. 6 confirms this finding by flow cytometry, and demonstrates retention of other markers of pluripotency such as SSEA-3 and SSEA-4, with negligible retention of the differentiation marker SSEA-1.

Figure 2:
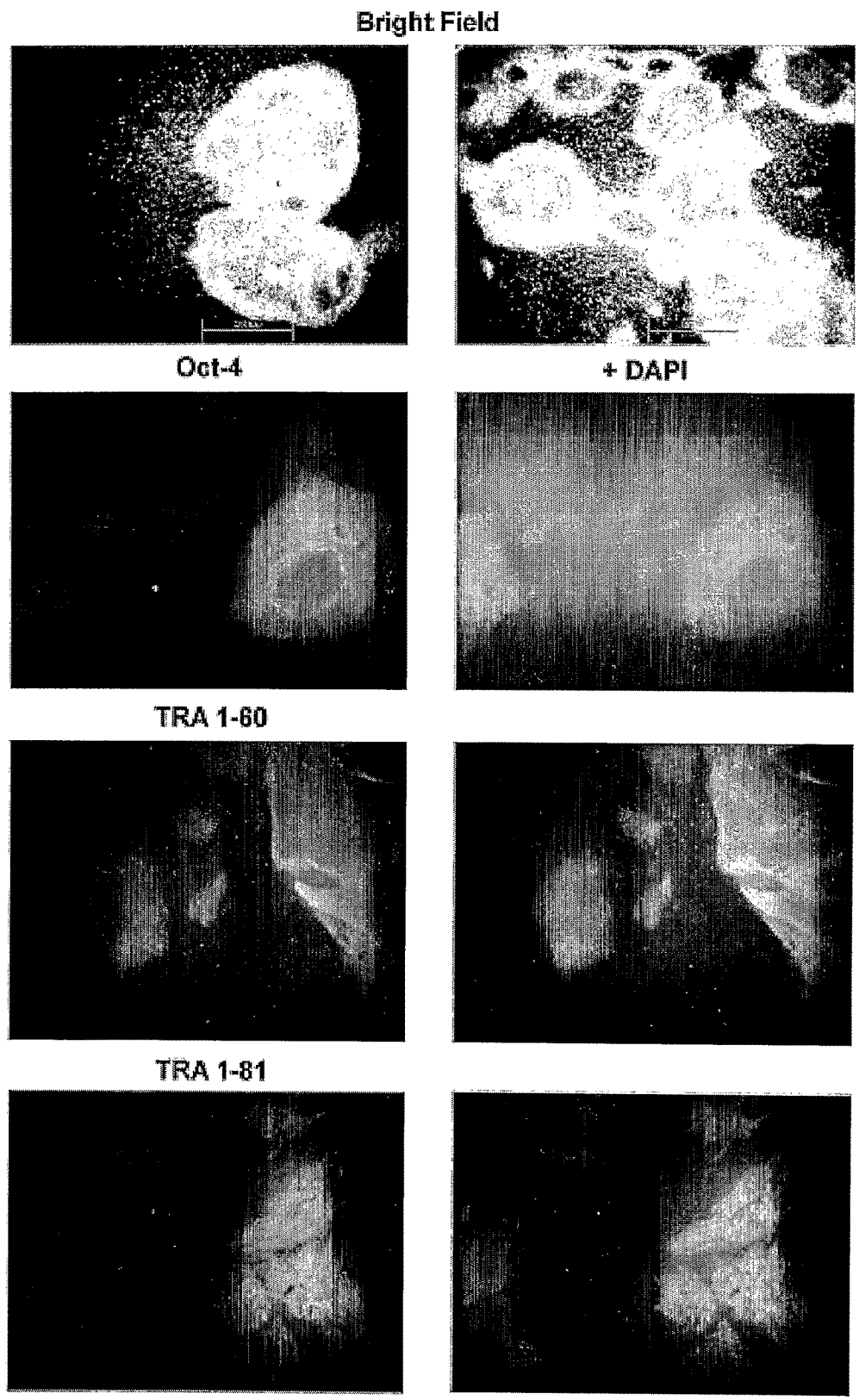
FIG. 2 shows post-frozen/thaw hESC culture maintained through multiple passages. Representative photomicrographs of bright field images (left and right panels represent replicate cultures) and Oct-4, TRA 1-60 and TRA 1-81 labelling of post frozen/thaw hES-2 cells illustrate recovery following freezing, thaw and reculture.
Figure 7:
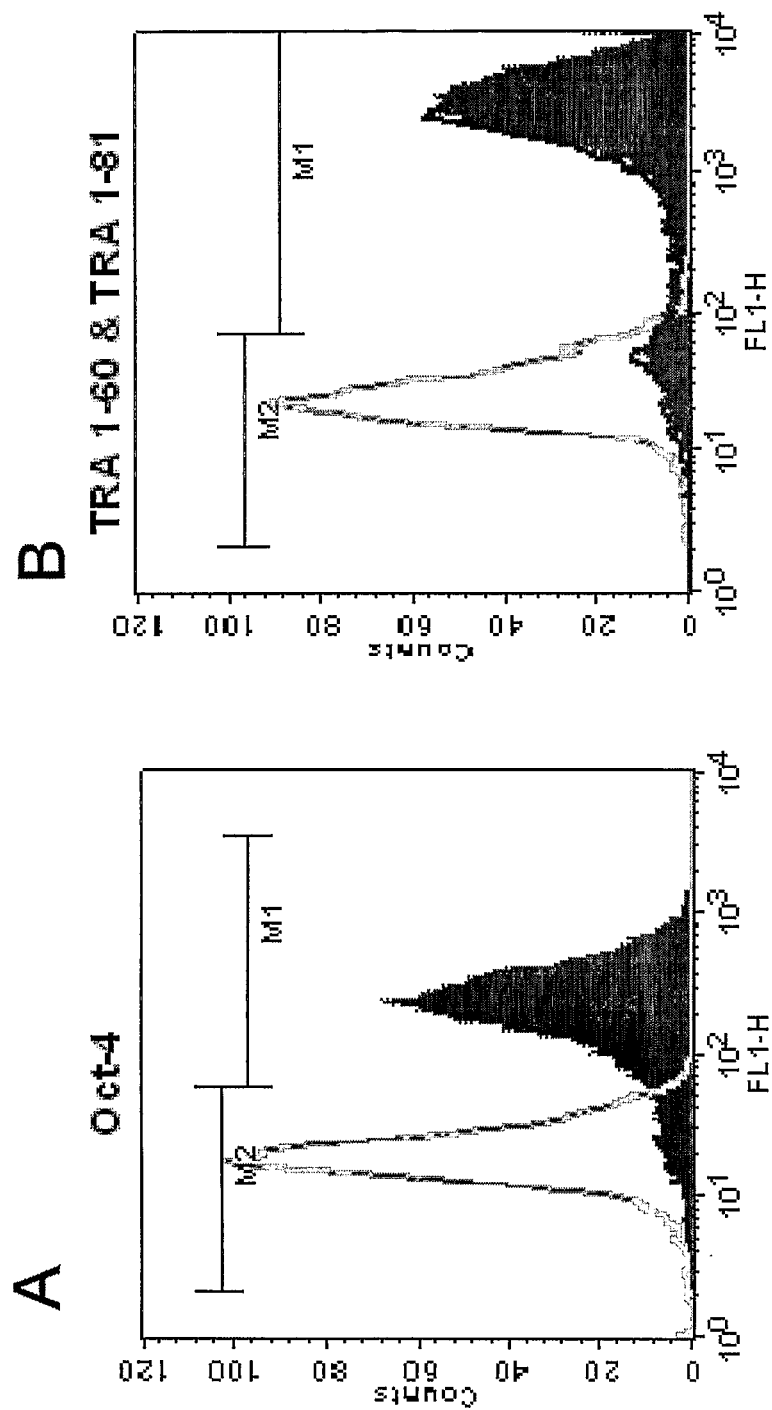
FIG. 7 shows flow cytometric analysis of post-frozen/thaw hESC recovery following 2 months storage in liquid nitrogen. Representative histogram plots derived from gated events of flow cytometry, illustrates cell number (Y-axis) and Oct-4, TRA 1-60, TRA 1-81, SSEA-3, SSEA-4 and SSEA-1 labelling (X-axis) of hES-2 cells following freezing, thaw and reculture.
Figure 7:
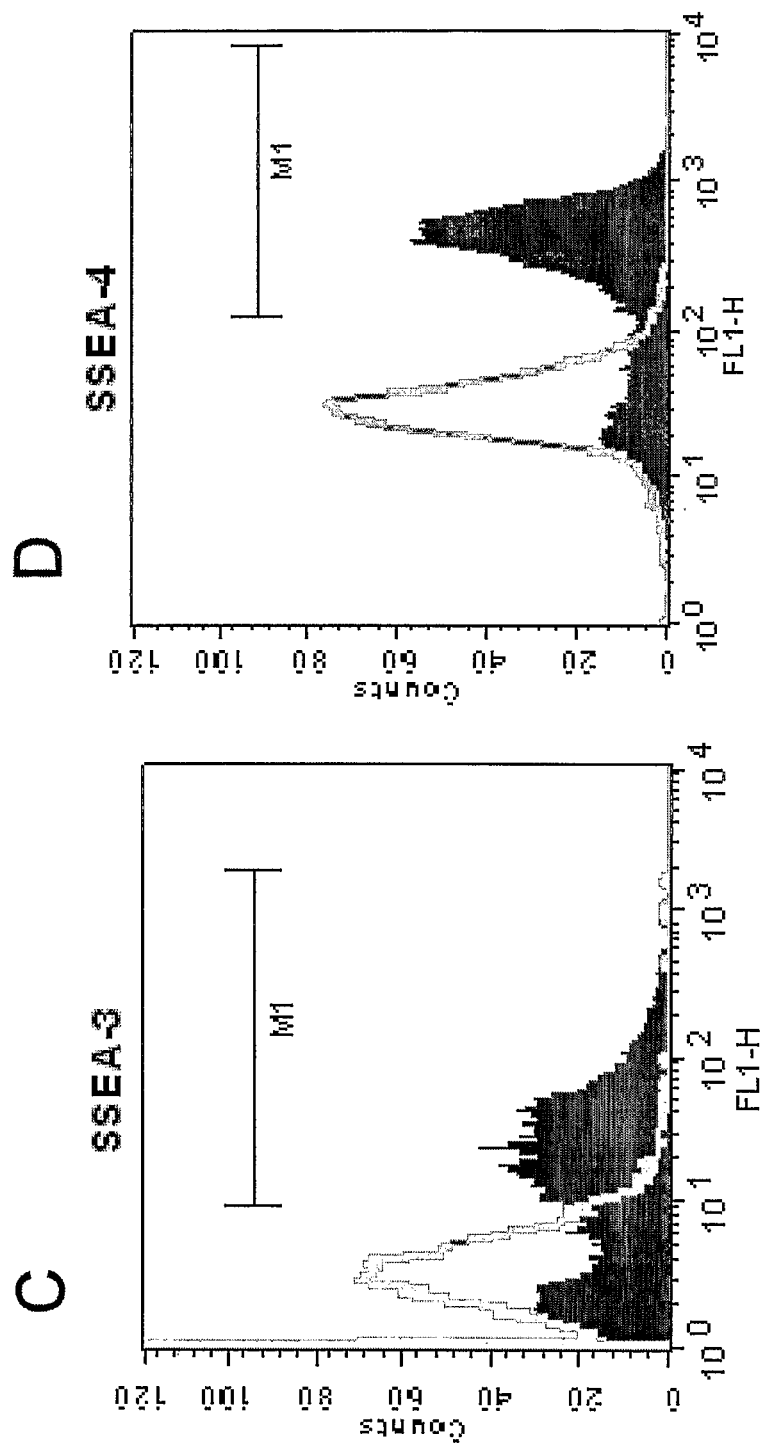
Figure 7:
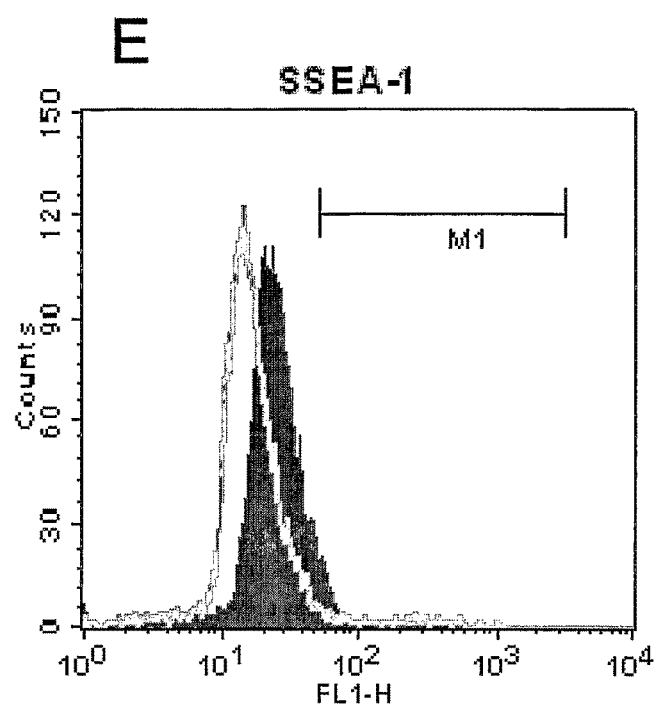

Of further significance, Applicants have shown that when passaged under appropriate conditions the thawed cells were able to maintain pluripotency. FIG. 2 shows that after five passages, the cells retained markers Oct-4, TRA 1-60 and TRA 1-81. FIG. 7 illustrates a flow cytometric analysis of hESCs whereby the cells maintained markers such as Oct-4, TRA 1-81, TRA 1-60, SSEA-3, SSEA-4, these markers being indicative of the pluripotency of a cell, while expressing negligible SSEA-1, a marker of differentiation.

Cells prepared and cryopreserved according to the methods described herein have the ability to differentiate in vivo into an endodermal, mesodermal or ectodermal cell. In a more preferred form of the invention the cells can differentiate into a cell type selected from the group consisting of an hepatic cell, a renal cell, a dermal cell, a cardiovascular cell, a neural cell, a skeletal cell, a pancreatic cell and a reproductive cell. Most preferably the cells can differentiate into a cell type selected from the group including a gut epithelial cell, a chondrocyte, an osteocyte and a hair follicle cell (see FIG. 9) The ability to differentiate in vitro has also been shown in FIG. 10 where hES-3 cells were differentiated into beta-like cells. The skilled person will have sufficient knowledge to direct a stem cell down a certain lineage as desired by exposing the cell to one or more culture conditions or agents.

Figure 3:
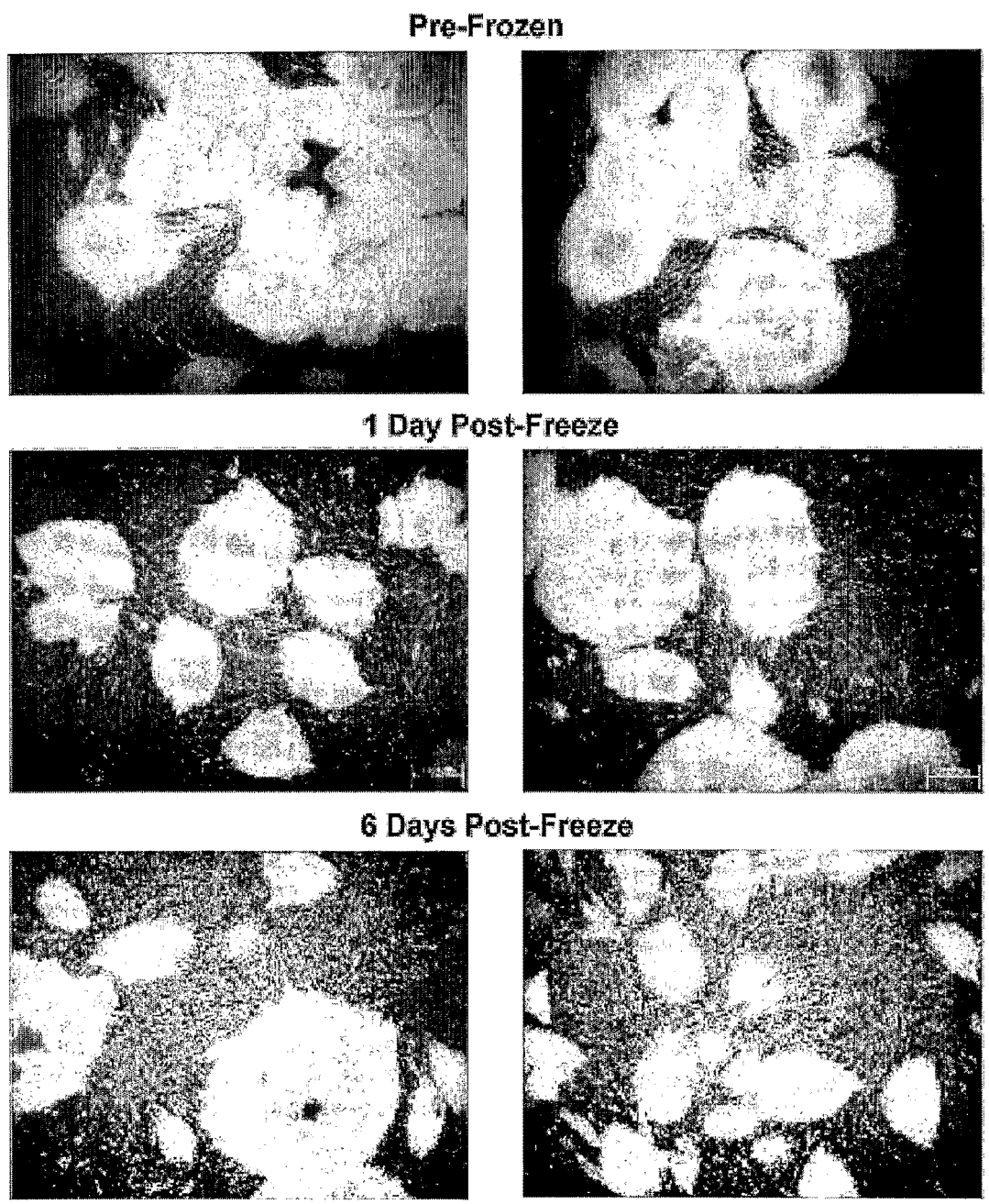
FIG. 3 shows post-frozen/thaw hESC recovery following short or longer term cryostorage. Representative photomicrographs of pre and post frozen/thaw hES-2 cells illustrate cell recovery following freezing, thaw and reculture. Left and right panels represent replicate cultures.

A further advantage of the invention is that cells do not appreciably degrade according to the length of storage. FIG. 3 shows that cells stored for 1 day or 6 days are of the same quality when thawed. In addition, FIG. 7 shows cells stored for 2 months remain of high quality and pluripotent.

While the cryopreservation of cell types hES-2, hES-3 and hES-4 has been demonstrated herein, the method is proposed to be applicable to the broader class of stem cells, including but not limited to embryonic stem cells and more particularly human embryonic stem cells. FIG. 6 shows that cell quality after freezing and thawing is equivalent for hES-2, hES-3 and hES-4 cells. Cytogenetic analysis of the three cell types revealed normal karyotypes. The Table below shows data on cytogenetic analysis of post-frozen/thaw hESCs—Normal karyotype of post frozen/thaw hES-2, hES-3 and hES-4, illustrating cell recovery following freezing, thaw and reculture.

| hESC Line | Replicate Study | Result |
| --- | --- | --- |
| hES-2 | 1 | 46XX |
|  | 2 | 46XX |
| hES-3 | 1 | 46 XX |
|  | 2 | 46XX |
| hES-4 | 1 | 46 XY |
|  | 2 | 46 XY |

Figure 8:
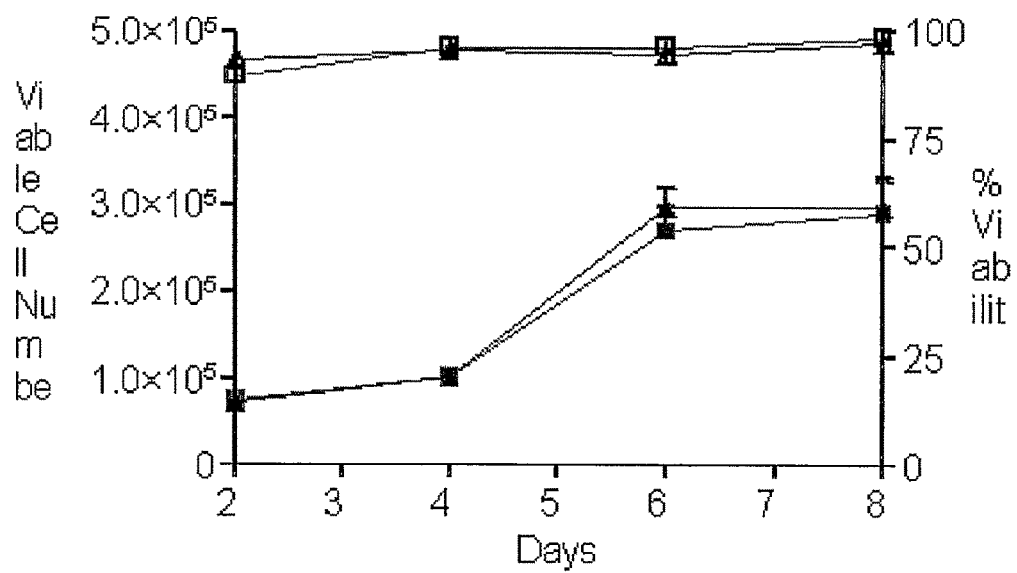
FIG. 8 shows a determination of growth rates of post-frozen/thawed hESCs. Representative growth profiles of post frozen/thaw hESCs, illustrating recovery with normal doubling rates (Study 1: ■/□, $t_d$=35 hr; Study 2: ▲/△, $t_d$=31 hr) following freezing, thaw and reculture. Viable cell numbers are represented by filled symbols, and % viability of total cells counted by open symbols. Each point represents the mean±SEM of three determinations. Each profile represents a replicate study.

The cells also exhibit normal growth rates after cryopreservation and thawing, as demonstrated by FIG. 8, which shows normal doubling rates for thawed cells.

Figure 11:
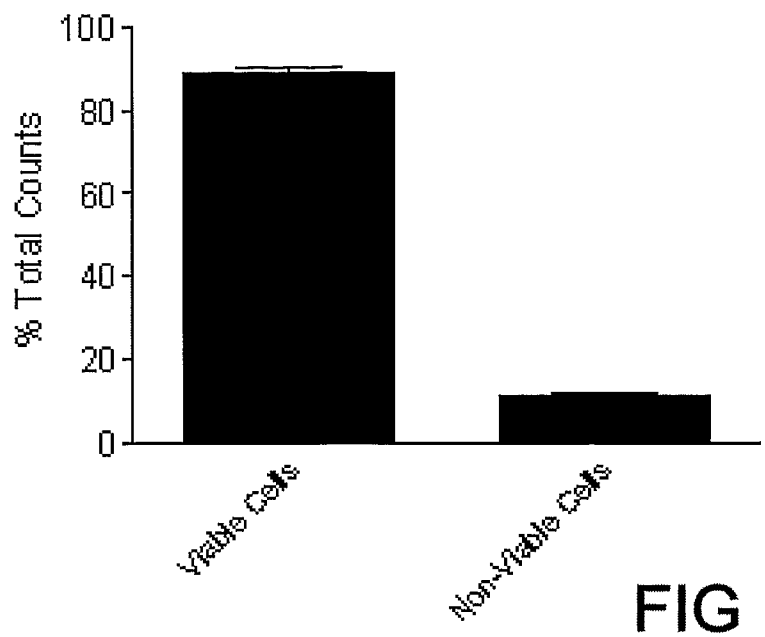
FIG. 11 shows post-frozen/thaw recovery of differentiated hESCs. Representative data of post-freeze/thaw illustrates viability of differentiated cells derived by formation of embryoid bodies (EBs) from hESCs together with a cardiomyocyte differentiation protocol.

The methods of the present invention are also applicable to cells derived from ES cells, such as progenitor cells, hepatic cells, renal cells, dermal cells, cardiovascular cells, neural cells, skeletal cells, pancreatic cells and reproductive cells. It is within the ability and knowledge of a person of ordinary skill in the art to produce a more differentiated cell for cryopreservation from a stem cell. FIG. 11 shows that progenitor cells derived from hESCs are able to be cryopreserved, thawed and then differentiated into cardiomyocyte-like cells. This is a significant contribution to the art since for the first time it is possible to harvest a stem cell from a subject, cryopreserve the cell, and thaw the cell at some time in the future for use in that subject or another subject without a substantial loss of cell quality. Before filing of this application, the art was dependent on methods that resulted in substantial loss of cell viability leading to a significant loss of cells. While a small number of cells survive the cryopreservation methods of the prior art, it was necessary to multiply passage the surviving cells to generate a number of cells useful for therapy. As the skilled person understands, multiple passaging is undesirable given the increased opportunity for the introduction of mutations in the cell genome. Furthermore, the inclusion of a biologically-derived material as a cryoprotectant necessarily increases the danger of exposing the subject to an adventitious pathogen As the skilled person will understand, the ability to more effectively cryopreserve stem cells is key to the further development of stem cells as therapeutics in the treatment of disease. In order to properly utilise a stem cell as a therapeutic in routine medical practice it will be necessary to provide a large bank of stem cells, the cells in the bank being derived from a single cell population. It is only by this approach that the physician can be assured of the origin, safety and efficacy of any stem cell used in therapy.

The method may be conducted in any apparatus capable of achieving the temperatures and rates of cooling required. Generally speaking, a purpose-built programmable biological rate freezer is the most suitable contrivance. An exemplary freezer is the MC-012 Planer Biological Freezer (Cat No Kryo 10-16 or Kryo 360-1.7). The use of computer controlled devices provides a high degree of reproducibility and therefore minimal batch-to-batch variation.

The cell suspension may be provided in any suitable receptacle for the purposes of the instant invention. The size of the receptacle may be such so as to facilitate rapid freezing of the sample contained therein, using methods of the present invention. Furthermore, the receptacle is likely be made of a material that will permit cold or heat to be rapidly conducted from an outer surface of the receptacle to the sample contained within the receptacle. In particular embodiments of the present invention, the material may also permit storage of the frozen sample at temperatures less than $-130°$ C. including, but not limited to, a temperature in the order of $-190°$ C. to $-200°$ C. An exemplary material that may be used under these conditions is polypropylene. Polypropylene has been used in known cryopreservation receptacles, for example cryotubes. In further embodiments of the present invention, the thickness of the walls of the receptacle will be sufficiently thin to permit rapid freezing of the sample contained therein, using methods of the present invention. A receptacle that may be used in particular embodiments of the present invention may include, but not be limited to, a straw such as a straw used in cell or embryo freezing. The receptacle may also be closeable by any means, including but not limited to heat sealing of its ends. An advantage of the present invention is that it is possible to conduct the freezing process with or without the receptable closed since it is not necessary to monitor a biophysical parameter of the cell suspension during freezing. For the purposes of maintaining sterility of the cell suspension, it is generally preferred to conduct the method with the receptacle closed.

The skilled artisan will be familiar with many such receptacles capable of withstanding the very low temperatures required for the cryopreservation of cells, with an example being MC-009 CBS High Security Straw Sterile (Cryo Bio System Cat No 014651). The straws may be closed by the manual sealing unit MC-010 SYMS (Cryo Bio Systems Cat No 007213) for CBS straws. The presently described exemplary straws are FDA approved for utilization in cell therapy and tissue engineering arena.

In another aspect the present invention provides a frozen cell, wherein the cell has been frozen according to a method as described herein.

A further aspect of the present invention provides a thawed cell, wherein the thawed cell has previously been frozen according to a method as described herein. Thawing of the cell can be accomplished by any suitable method known to the skilled artisan. In a preferred embodiment the cells are rapidly brought to 37° C. by submerging the receptacle containing the cell suspension in a water bath. Once the suspension is thawed, the cells may be pelleted and washed in any suitable medium. On many occasions it will be advantageous to resuspend the cells in the media required for further culturing of the cells.

In another aspect the present invention provides a method of treating a subject in need of a stem cell transplant, the method including administering to the subject an effective amount of a frozen or thawed cell as described herein. There are a number of diseases that may be treated by the administration of stem cells with promising areas including neurodegenerative disorders, heart disease and diabetes.

In another aspect the present invention provides a method of growing an organ or tissue in vitro, the method including use of a frozen or thawed stem cell as described herein. Stem cells may be used to manufacture complete organs, parts of organs, or tissues for subsequent implantation into a subject. For example stem cells may be used to generate skin grafts for use on burns victims. Stem cells may also be used to generate entire organs such as the pancreas. This would have use in the treatment of insulin dependant diabetes mellitus.

Given the therapeutic utility of ES cells, it will be clear that the cells of the present invention will have use in the form of a pharmaceutical composition. Accordingly, the present invention provides a pharmaceutical composition including a frozen or thawed cell as described herein in combination with a pharmaceutically acceptable carrier. The skilled person will be familiar with many substances that may be combined with the cells of the present invention to enhance stability and viability of the cells in the composition. As an example, substances such as buffers and salts may be added to adjust the pH and tonicity of the composition as a whole.

In another aspect the present invention provides the use of a frozen or thawed cell as described herein in the preparation of a medicament for the treatment or prevention of a condition requiring a stem cell transplant.

Examples of the methods used in the present invention will now be more fully described. It should be understood, however, that the following description is illustrative only and should not be taken in any way as a restriction on the generality of the invention described above.

EXAMPLES

Example 1

Preparation and Cryopreservation of hESCs

The methods were performed in a laboratory having standard cell biology equipment (biosafety hoods, pipettes, aspiration pumps, 5% $CO_2$ incubator at 37° C., 70% ethanol spray, centrifuge, tubes, dissecting microscope with warm stage, liquid nitrogen storage vessel etc). Before commencing the methods, the following reagents were prepared: live hESC colonies, hESC culture media (hESC media), Phosphate Buffered Saline (PBS; Gibco catalogue number 14040-133), Collagenase IV (20 mg/ml stock prepared in-house; Serva catalogue number 17458.03), Dimethylsulfoxide (DMSO; Sigma-Aldrich product number D1435/D2650), and CRYOSTOR CS5™ Cryopreservation Solution (BioLife Solutions catalogue number 99-610-DV). The hESC media consisted of 20% KnockOut Serum Replacement comprising bovine serum albumin (Invitrogen/Gibco, catalogue number 04-0095) or human serum albumin, 78% KnockOut DMEM (Invitrogen/Gibco, catalogue number 10829-018), 1% L-Glutamine (Invitrogen/Gibco, catalogue number 25030-081), 1% NEAA (Invitrogen/Gibco, catalogue number 11140-050), and 50 ng/mL bFGF (Strathmann Biotech AG, catalogue number 9511060).

The following specialised hardware was provided in the laboratory: CBS High Security Straw Sterile (Cryo Bio System catalogue number 014651), SYMS manual sealing unit for CBS straws (Cryo Bio Systems catalogue number 007213), a Planer Biological Freezer (catalogue number Kryo 10-16 or Kryo 360-1.7).

Cells were harvested using Collagenase IV. Briefly, media was aspirated from cell culture vessels containing hESCs and rinsed with PBS+. Collagenase IV working solution was added to cell culture vessels and incubated at 37° C., 5% $CO_2$ for 8-10 min. hESCs were gently scraped from the culture surface and hESC media was added and the cell suspension was gently agitated.

Digested cell clumps (variable size) were transferred to a tube with hESC media and disaggregated further to generate more uniform cell clumps. Cells were then pelleted by centrifugation.

Media was aspirated and each cell pellet resuspended in freezing solution. Cells were maintained in freezing solution on ice for 10 min.

Cells in freezing solution were transferred to CBS™ High Security Straws using a P200. Each straw was held at the top, where the safety stopper ensured that sterility was maintained throughout the filling procedure. The open end of a straw was protected from any contamination. The ends of a loaded straw were carefully sealed using the sealing unit. Straws were labelled and maintained on ice until all "loaded" straws were sealed.

Once the freezing chamber of the control rate freezer had reached the start temperature (+4° C.), straws were loaded into the unit. "Run" was selected from the main menu.

For manual ice nucleation at −8° C., after soaking the cells at −8° C. for 5 min: the cells were ice nucleated by application of liquid nitrogen cooled forceps to the outside of the straws. "Enter" was pressed on the control rate freezer control panel to resume the profile. Where "Automated" ice nucleation of the cells was implemented a rapid cooling ramp program was used (for example program see the table in Example 3).

Straws were then removed from the control rate freezer and plunged to liquid nitrogen, where they were stored in a liquid nitrogen vessel_canister.

Example 2

Freezer Program Incorporating Manual Ice Nucleation

The following program was used with a Planer Biological Rate Freezer and included a manual ice nucleation step.

| STEP (RAMP) | FROM (° C.) | TO (° C.) | RATE (° C./MIN) | TIME (MIN) | DESCRIPTION |
|---|---|---|---|---|---|
| 1. | +4 | +4 | 0 | 5 | HOLD |
| 2. | +4 | -8 | -1.0 | | Cold activation |
| 3. | -8 | -8 | 0 | 5 | Soak |
| 4. | -8 | -8 | 0 | | Manual ice nucleation |
| 5. | -8 | -8 | 0 | 5 | Hold after ice nucleation |
| 6. | -8 | -38 | -0.8 | | Dehydration |
| 7. | -38 | -100 | -10.0 | | Pre-plunge rapid cool |
| 8. | -100 | -180 | -35.0 | | Plunge |

Example 3

Freezer Program Incorporating Automated Ice Nucleation

The following freezing program was used with a Planer Biological Rate Freezer, and including a automatic ice nucleation step.

| STEP (RAMP) | FROM (° C.) | TO (° C.) | RATE (° C./MIN) | TIME | DESCRIPTION |
|---|---|---|---|---|---|
| 1. | +4 | +4 | 0 | 5.00 min | HOLD |
| 2. | +4 | -8 | -1.0 | | Cold activation |
| 3. | -8 | -8 | 0 | 5.00 min | Soak |
| 4. | -8 | -10.9 | -38.0 | | Auto ice nucleation |
| 5. | -10.9 | -12.1 | -9.0 | | Auto ice nucleation |
| 6. | -12.1 | -12.1 | 0 | 0.02 sec | Hold after auto ice nucleation |
| 7. | -12.1 | -11.9 | +21.0 | | |
| 8. | -11.9 | -12.0 | -1.0 | | |
| 9. | -12.0 | -12.0 | 0 | 1.00 min | HOLD |
| 10. | -12.0 | -38 | -0.8 | | Dehydration |
| 11. | -38 | -100 | -10.0 | | Pre-plunge rapid cool |
| 12. | -100 | -180 | -35.0 | | Plunge |

(Steps 4–10 bracketed as "Auto ice nucleation")

Example 4

Thawing hESCs

A hESC loaded straw was removed from liquid nitrogen to a portable receptacle containing liquid nitrogen. The straw was thawed immediately by gently swirling in a 37° C. water bath until only a small ice pellet remained (10-20sec).

The straw was completely submerged in 70% ethanol. Once dry, the end of the straw was cut off about 0.5 cm from the hydrophobic plug, using a sterile scalpel or pair of scissors. The other end of the straw was cut off above the seal.

The contents of the straw were emptied into a conical centrifuge tube with 37° C. hESC media. The straw was then rinsed with an additional volume of hESC media. The cells were centrifuged at 1000rpm for 3 min, the supernatant was aspirated, and the cell pellet resuspended in 37° C. hESC media. The cell suspension was transferred to prepared cell culture vessels containing 37° C. hESC media for subsequent culture Example 5

Effect of Cryopreservation on Cellular Parameters

In order to show the general quality of frozen and thawed cells, hESCs were cultured on human fibroblast feeder cells in hESC media, enzymatically disaggregated with Collagenase IV, contained in hermetically sealed straws and frozen. After storage in liquid nitrogen, cell samples were thawed and re-cultured for 8 days. FIG. 1 demonstrates that recovered hESCs were healthy, robust and undifferentiated (non-cystic and immunopositive) cell growth, supporting the efficacy of the cryopreservation protocol employed.

To be useful in the laboratory and clinic, it was necessary to show that the cryopreservation method did not affect the ability of cells to be maintained through multiple passages. Briefly, hESC colonies were cultured on human feeders in hESC media, enzymatically disaggregated with Collagenase IV, contained in hermetically sealed straws and frozen. After storage for 6 days in liquid nitrogen, cell samples were thawed and re-cultured through 5 passages. It can be noted from the micrographs in FIG. 2 that hESC colonies comprised healthy, robust and undifferentiated (non-cystic and immunopositive) cell growth, supporting the efficacy of the cryopreservation protocol employed.

Figure 4:
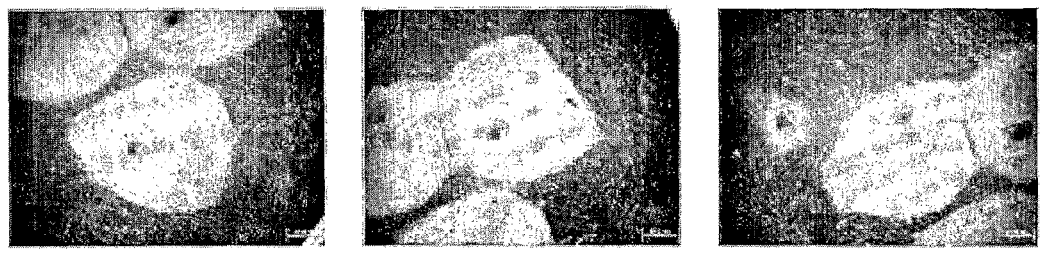
FIG. 4 shows post-frozen/thaw hESC recovery with mechanical cell passaging. Representative photomicrographs of pre and post frozen/thaw hES-2 cells illustrate cell recovery following freezing, thaw and reculture. Panels represent replicate cultures

To demonstrate that the time of cryostorage did not adversely affect cells when frozen using the cryopreservation method, hESCs were cultured on human fibroblast feeder cells in hESC media, enzymatically disaggregated with Collagenase IV, contained in hermetically sealed straws, frozen and stored for short (1 day) and longer (6 days) term. After storage for 1 day or 6 days in liquid nitrogen, cell samples were thawed and re-cultured for 11 days. FIG. 3 shows that hESC recovery comprised healthy, robust and undifferentiated/non-cystic cell growth, supporting the efficacy of the cryopreservation protocol employed. In a further example, FIG. 7 shows cells stored for 2 months or longer remain of high quality and pluripotent, confirming the efficacy of extended term storage using the present cryopreservation method The effect of mechanical cell passage in combination with the inventive methods was also assessed. hESCs were cultured on human fibroblast feeder cells in hESC media, mechanically disaggregated, contained in hermetically sealed straws and frozen. After storage in liquid nitrogen, cell samples were thawed and re-cultured for 15 days. FIG. 4 shows recovered hESCs were healthy, robust and undifferentiated/non-cystic, supporting the efficacy of the cryopreservation protocol employed.

Figure 5:
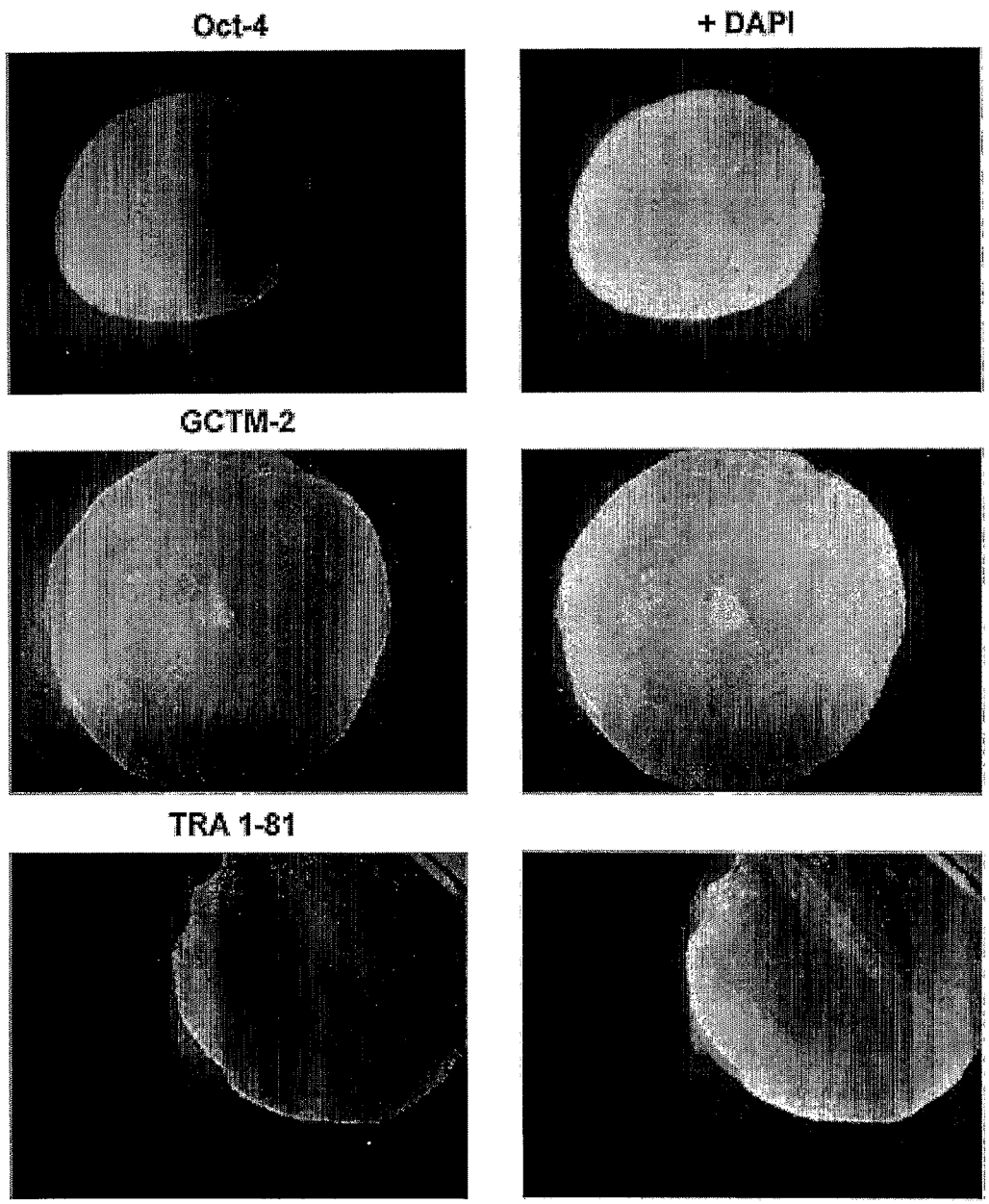
FIG. 5 shows post-frozen/thaw hESC recovery with mechanical cell passaging. Representative photomicrographs of post frozen/thaw hES-2 cells, illustrate GCTM-2, Oct-4 and TRA 1-81 labelling following freezing, thaw and reculture.

FIG. 5 provides further support for the utility of mechanical passaging. hESCs were cultured on human fibroblast feeder cells in hESC media, enzymatically disaggregated with Collagenase IV, contained in hermetically sealed straws and frozen. After storage in liquid nitrogen, cell samples were thawed and re-cultured through 1 passage using mechanical transfer. Clearly, hESC recovery comprised healthy, robust and undifferentiated (immunopositive) growth, supporting the efficacy of the cryopreservation protocol employed.

The effect of multiple passaging in combination with mechanical disaggregation was assessed. hESCs were cultured on human fibroblast feeder cells in hESC media, mechanically disaggregated, contained in hermetically sealed straws and frozen. After storage in liquid nitrogen, cell samples were thawed and re-cultured through 5 passages again using mechanical transfer. Immunohistochemistry was performed on day 7 cultures following passage 5. Clearly, hESC recovery comprised healthy, robust and undifferentiated (immunopositive) cell growth, supporting the efficacy of the cryopreservation protocol employed (see FIG. 6).

FIG. 7 further shows that the cryopreservation method does not affect the expression of differentiation-related cellular markers. hESCs were cultured on human fibroblast feeder cells in hESC media, mechanically disaggregated, contained in hermetically sealed straws and frozen. After storage in liquid nitrogen, cell samples were thawed and re-cultured. Relative to negative control (i.e. Isotype antibody labelling; left hand green open plots), most cells sustained high level Oct-4 (~90%; pink filled), TRA1-60 (~90%; pink filled), TRA 1-81 (~90; blue open), SSEA-3 (60%; pink filled), SSEA-4 (~70%; pink filled), and negligible SSEA-1 (~5%; pink filled) expression, indicating undifferentiated hESC proliferation. Clearly, data support hESC recovery comprising undifferentiated (immunopositive) cell growth, supporting the efficacy of the cryopreservation protocol employed.

The effect of freezing and thawing on growth rates of hESCs was investigated. hES-2 cells were cultured on human fibroblast feeder cells in hESC media, enzymatically disaggregated with Collagenase IV, contained in hermetically sealed straws and frozen. After storage in liquid nitrogen, cell samples were thawed and re-cultured through >9 passages. Viable cell number was identified during the exponential growth phase of the final week of culture. Cells were harvested daily using Collagenase IV and viable cell numbers were determined by Trypan blue exclusion for calculation of doubling time and plotting as graphs of number verses time. For all studies, cultures comprised high cell viability and reached confluency within the time period studied. The data presented in FIG. 8 confirms hESC recovery comprising normal growth, supporting the efficacy of the cryopreservation protocol employed.

The effect of freezing and thawing on cell karyotype was investigated. Briefly, hESCs were cultured on human fibroblast feeder cells in hESC media, mechanically disaggregated, contained in hermetically sealed straws and frozen. After storage in liquid nitrogen, cell samples were thawed, re-cultured through a minimum of 5 passages and harvested. Normal cell karyotype was determined by evaluating Giemsa stained metaphase spreads, supporting the efficacy of the cryopreservation protocol employed. Replicate studies represent separate cell cultures performed in parallel.

Figure 9:
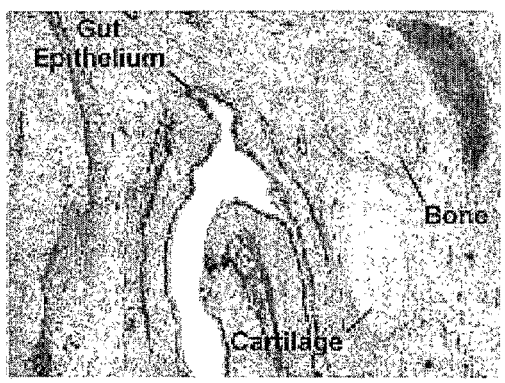
FIG. 9 shows in vivo differentiation of post-frozen/thaw hESCs. Representative photomicrographs illustrate teratoma sections, derived from xenografting of hES-2 cell clusters following freezing, thaw and reculture.
Figure 9:
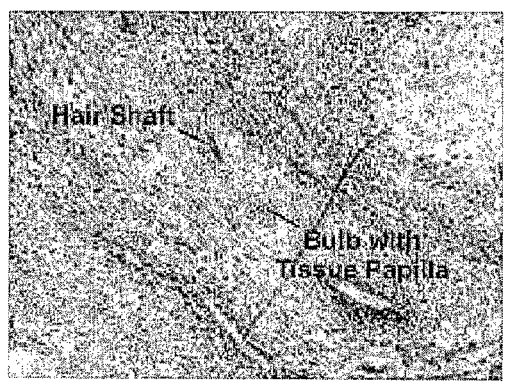
Figure 10:
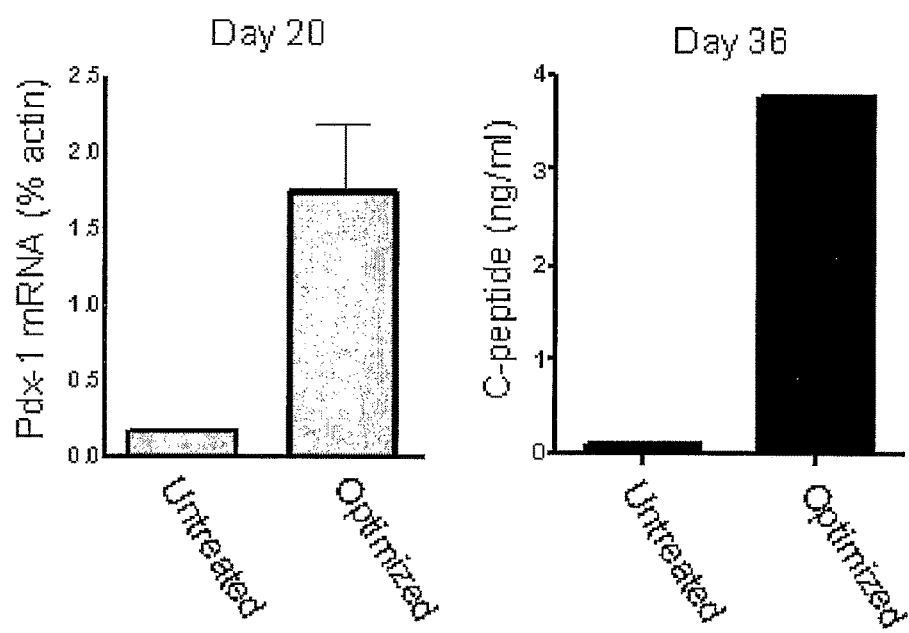
FIG. 10 shows in vitro differentiation of post-frozen/thaw hESCs. Representative data illustrates post-freeze/thaw differentiation of hESCs.

FIG. 9 presents further evidence that hESCs preserved by the present method maintain pluripotency and will differentiate in vivo, and will therefore be useful in the clinic. hESCs were cultured on human fibroblast feeder cells in hESC media, mechanically disaggregated, contained in hermetically sealed straws and frozen. After storage in liquid nitrogen, cell samples were thawed, re-cultured, harvested and grafted into the testes of severe combined immunodeficiency mice to generate teratomas. Histological analysis indicated that tumors comprised differentiated tissues of all three embryonic germ layers such as gut epithelium (endoderm), cartilage and bone (mesoderm), and hair follicles (ectoderm); supporting hESC pluripotency and the efficacy of the cryopreservation protocol employed.

In vitro differentiation of thawed hESCs was studied. hES-3 cells were thawed and expanded through 4 passages. The cells were then placed through a 36-day optimized beta-cell differentiation protocol and screened for the intermediate marker gene pdx-1 on day 20 (left panel), and for C-peptide release into the media on day 36 (right panel). Taken together, the data shown in FIG. 10 support the efficacy of the cryopreservation protocol employed for preservation of hESCs, able to be transformed after thawing to differentiated cell types such as beta-like cells.

In order to show that the method has utility for cells derived from hESCs, hES-3 derived embryoid bodies were enzymatically digested and disaggregated progenitor cells were split into two groups of samples, contained in separate batches of freezing media in hermetically sealed straws and frozen. After storage for 8 days in liquid nitrogen, cell samples were thawed, counted, plated and cultured to active cardiomyocytes by directed differentiation. Importantly, after freeze/thaw, the majority of cells attached, with beating cardiomyocytes apparent following 5 days of culture. Taken together, data shown in FIG. 11 support the efficacy of the cryopreservation protocol employed for preservation of hESC derived progenitor cells, able to be transformed to differentiated cells such as cardiomyocyte-like cells.

Efficacy of preparing cells for freezing is clearly an important feature of the method. This was evaluated by culturing hES-2 cells on mouse fibroblast feeder cells in hESC media, enzymatically disaggregating them with Collagenase IV, and suspending them in cryopreservation medium at 4° C. over 3 hours. Samples were taken from stock every 20 min, trypsinized and counted using trypan blue exclusion method. Data presented in FIG. 12 indicate a gradual but acceptable slow decrease in viable cells and corresponding increase in non-viable cells over the time period measured.

It will be apparent to the skilled person that many routines variations may be applied to the various methods and compositions described herein. It is intended that these variations are included with the scope of the present application.

The invention claimed is:
1. A composition comprising:
(a) adenosine, dextran-40, lactobionic acid, HEPES (N-(2-Hydroxyethyl) piperazine-N'-(2-ethanesulfonic acid)), sodium hydroxide, L-glutathione, potassium chloride, potassium bicarbonate, potassium phosphate, dextrose, sucrose, mannitol, calcium chloride, magnesium chloride, potassium hydroxide, sodium hydroxide, dimethyl sulfoxide (DMSO), and water; and

(b) pluripotent stem cells, wherein the composition can be stored at a temperature sufficiently low enough to allow long term storage of the pluripotent stem cells.

2. The composition of claim 1, wherein upon thawing, the pluripotent stem cells retain pluripotency.

3. The composition of claim 1, wherein the pluripotent stem cells are human embryonic stem cells.

4. The composition of claim 1, wherein upon thawing, the pluripotent stem cells are capable of differentiating into a cell type selected form the group consisting of a hepatic cell, a renal cell, a dermal cell, a cardiovascular cell, a neural cell, a skeletal cell, a pancreatic cell and a reproductive cell.

5. The composition of claim 1, wherein upon thawing, the pluripotent stem cells are capable of differentiating into a cell type selected form the group consisting of a gut epithelial cell, a chondrocyte, an osteocyte, a cardiomyocyte-like cell, a beta-like cell, and a hair follicle cell.

6. The composition of claim 1, wherein the composition does not include an exogeneous biological cryoprotectant.

7. The composition of claim 1, wherein a cell parameter is substantially unchanged after thawing, the cell parameter including viability and/or the ability to differentiate under appropriate stimulus.

8. The composition of claim 1, wherein upon thawing, the pluripotent stem cells have a viability of up to approximately 90%.

9. The composition of claim 1, wherein upon thawing, the pluripotent stem cells retain an undifferentiated phenotype.

10. The composition of claim 1, wherein upon thawing, the pluripotent stem cells exhibit non-cystic growth.

11. The composition of claim 1, wherein upon thawing, the pluripotent stem cells retain at least one marker selected form the group consisting of Oct-4, TRA 1-60, TRA 1-81, SSEA-3, and SSEA-4.

12. The composition of claim 1, wherein upon thawing, the pluripotent stem cells exhibit negligible retention of the marker SSEA-1.

13. The composition of claim 1, wherein upon thawing, the pluripotent stem cells are capable of differentiating in vivo or in vitro into an endodermal, mesodermal, or ectodermal cell.

14. The composition of claim 1, wherein the pluripotent stem cells which are stored frozen for at least 2 months retain pluripotency.

15. The composition of claim 1, wherein upon thawing, the pluripotent stem cells exhibit a normal karyotype.

16. The composition of claim 1, wherein upon thawing, the pluripotent stem cells exhibit a normal growth rate.

17. The composition of claim 1, wherein the temperature is about −180° C.

18. The composition of claim 1, wherein the temperature is less than about −130° C.

19. The composition of claim 1, wherein the temperature is between about −190° C. to −200° C.

\* \* \* \* \*